United States Patent
Oden et al.

(10) Patent No.: US 8,535,277 B2
(45) Date of Patent: Sep. 17, 2013

(54) METHOD AND APPARATUS FOR DOSE MEASUREMENT

(75) Inventors: Maria Oden, Houston, TX (US); Julia Ellen Davidson Lukomnik, New York, NY (US); Cindy M. Dinh, Houston, TX (US); Amanda Michelle Guiterrez, Houston, TX (US); Carlos Amaro, Houston, TX (US); Rebecca R. Richards-Kortum, Houston, TX (US)

(73) Assignee: William Marsh Rice University, Houston, TX (US)

( * ) Notice: Subject to any disclaimer, the term of this patent is extended or adjusted under 35 U.S.C. 154(b) by 118 days.

(21) Appl. No.: 13/052,974

(22) Filed: Mar. 21, 2011

(65) Prior Publication Data

US 2012/0245530 A1 Sep. 27, 2012

(51) Int. Cl.
*A61M 5/00* (2006.01)
(52) U.S. Cl.
USPC .................. 604/208; 604/189; 604/220
(58) Field of Classification Search
USPC ......................... 604/189, 208, 220
See application file for complete search history.

(56) References Cited

U.S. PATENT DOCUMENTS

| | | | | |
|---|---|---|---|---|
| 2,959,170 A | * | 11/1960 | Laub | 604/220 |
| 4,267,846 A | * | 5/1981 | Kontos | 600/578 |
| 5,300,042 A | | 4/1994 | Kossoff et al. | |
| 5,370,621 A | * | 12/1994 | Godat et al. | 604/199 |
| 5,975,355 A | * | 11/1999 | Cecala et al. | 222/43 |
| 7,452,350 B2 | | 11/2008 | Yeakley | |
| 2002/0087121 A1 | * | 7/2002 | Slishman | 604/189 |
| 2004/0059300 A1 | * | 3/2004 | Kosinski et al. | 604/213 |
| 2005/0119622 A1 | * | 6/2005 | Temple | 604/189 |
| 2005/0215957 A1 | * | 9/2005 | Hynes | 604/218 |
| 2008/0281274 A1 | * | 11/2008 | Rolla | 604/200 |

\* cited by examiner

*Primary Examiner* — Emily Schmidt
(74) *Attorney, Agent, or Firm* — Fletcher Yoder, P.C.

(57) ABSTRACT

The present disclosure relates to devices for use in conjunction with a syringe in measuring a dose using the syringe. In certain embodiments, a clip is provided that includes an elongated portion for insertion into a barrel of a syringe and a locking portion that locks onto a feature of the syringe. Once inserted, the clip physically prevents retraction of a plunger of the syringe past a certain point corresponding to a desired dose.

15 Claims, 7 Drawing Sheets

METHOD AND APPARATUS FOR DOSE MEASUREMENT

BACKGROUND

The present disclosure relates generally to methods and devices for measuring a dose, such as of a medication or other liquid, using a syringe.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Syringes are often used in the oral administration of liquid medications to the pediatric population. In particular, a syringe may be partly filled with a dose of a medication and the syringe may then be inserted into the mouth of the child. The dose may then be dispensed from the syringe into the mouth of the child, where it is swallowed. In this manner, a prescription or over-the-counter medication may be administered to a pediatric patient who might otherwise be difficult to treat.

Syringes for use in administering pediatric medications may be used with over-the-counter medications (where the syringe may be provided in the packaging with the medication) or with prescription medications (where a pharmacist, doctor, or other medical professional may provide the syringe). Parents or guardians commonly administer such oral medications to their children using pharmacist or manufacturer provided syringes. For many medications, the patient receives recurring doses of the medication until such time as the course of treatment is completed or the medication is otherwise no longer needed.

However, while a syringe is convenient for administering oral medications, it is possible for an incorrect dose to be administered using such a syringe. In particular, measurement errors are possible in which the incorrect amount of medication is loaded into the syringe. Such errors may arise due to carelessness, fatigue, difficulty in reading markings provided on the syringe, misunderstanding of the proper dosage (or lack of familiarity with the dosage units), and so forth. As a result the patient being treated may not receive the proper amount of medication.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

The present disclosure relates to methods and devices that may be used to mechanically or physically stop a plunger of a syringe from retracting beyond a specified dosage point, thereby providing an indication of when the correct dose of a medication is contained within the syringe as well as preventing overfilling of the syringe beyond the specified dose. In one embodiment, a clip is provided that attaches to the syringe and extends partially into the barrel of the syringe. The clip, when secured, prevents a plunger of the syringe from retracting beyond a point associated with a given dose. In such embodiments, a variety of clips may be provided that correspond to different dosages for a given syringe type. The clip corresponding to a given dosage may be attached by a user of the syringe, such as a parent or guardian, or may be attached by a medical professional, such as a pharmacist or physician, prior to being given to the parent or guardian.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure relates to approaches for measuring and administering a specified dose using a syringe. In certain implementations, a clip is employed which is inserted at least partially into the barrel of a syringe and secured to the syringe, such as to a flange formed as part of the body of the syringe. When secured, the clip prevents the plunger from being withdrawn beyond a point corresponding to a specified or prescribed dose. In this manner, a person using a syringe with a clip attached may withdraw the plunger to fill the syringe until the clip physically prevents further withdrawal of the plunger. In this manner, the user can fill the syringe with the specified or prescribed dose.

Figure 1:
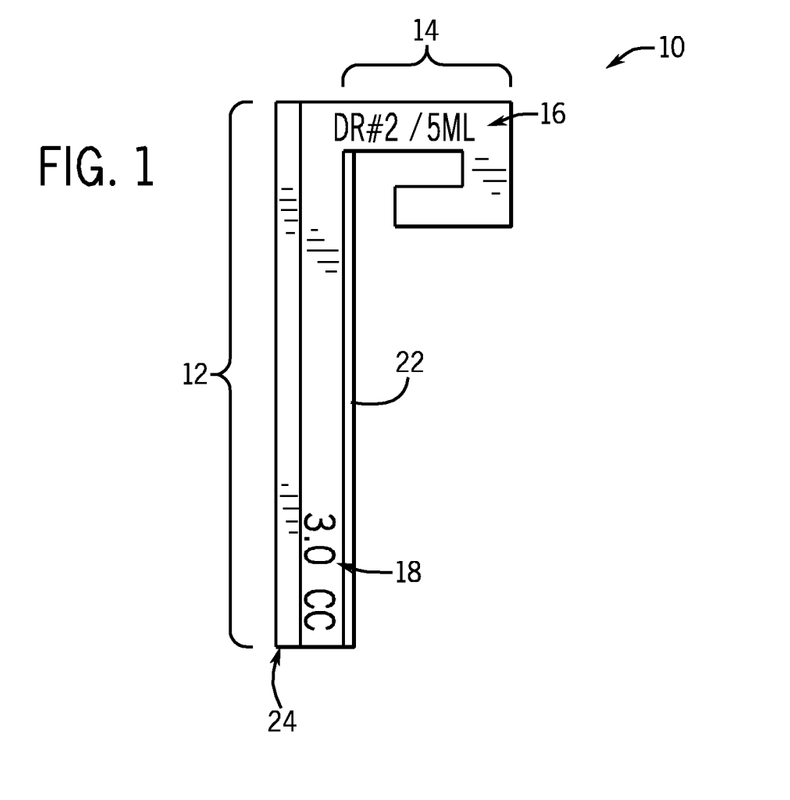
FIG. 1 depicts a plan view of one embodiment of a clip for use with a syringe, in accordance with aspects of the present disclosure.
Figure 2:
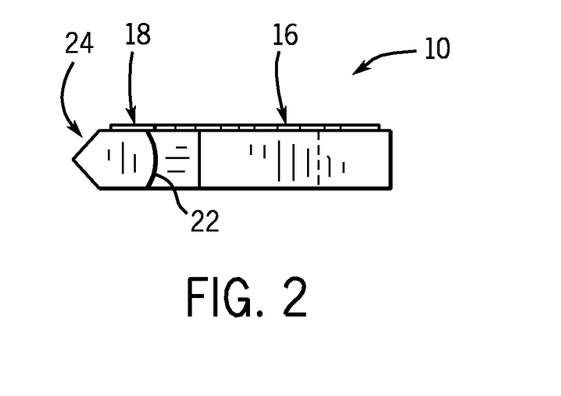
FIG. 2 depicts an end view of one embodiment of a clip for use with a syringe, in accordance with aspects of the present disclosure.
Figure 3:
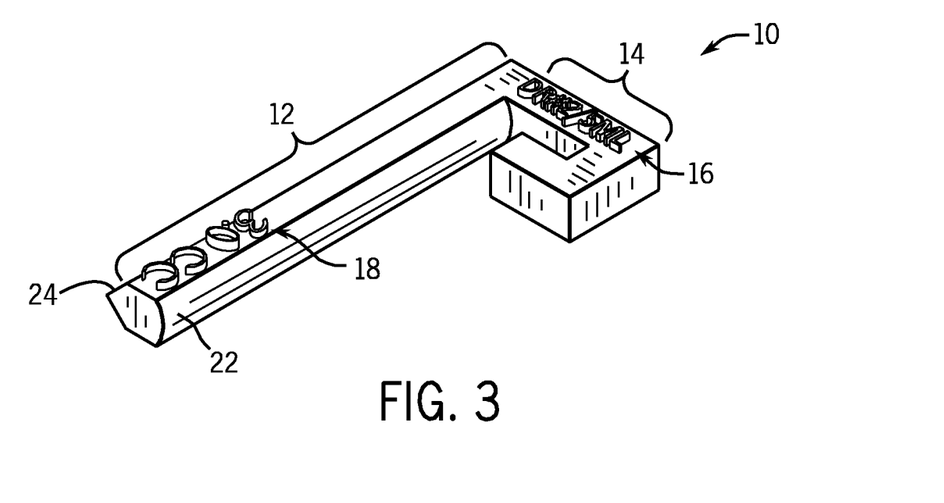
FIG. 3 depicts a perspective view of one embodiment of a clip for use with a syringe, in accordance with aspects of the present disclosure.

With the foregoing discussion in mind and turning to FIGS. 1-3, one embodiment of a suitable clip 10 is depicted by way of example. In this example, the clip 10 includes an elongated portion 12, which is configured to be inserted into the body of a suitable syringe, and a locking portion 14, which is configured to securely engage with a complementary structure of a syringe. In the depicted example, the locking portion 14 is provided as a C-clamp that may slidably or rotatably engage a feature of a syringe, such as a finger flange of the syringe. In certain embodiments, the locking portion 14 may be shaped or may include a visual indication to indicate the type or brand of syringes with which the clip 10 is to be used.

In certain implementations the clip 10 includes identifying information in the form of imprinted or raised text, such as an indication 16 of the type and/or size of syringe for which the clip 10 is sized and/or an indication 18 of the dose to which the clip 10 corresponds. Other information that may be indicated on the clip 10, such as by type or by other visual indicators (such as color coding) may include information relating to instructions or criteria for use of the respective clip 10. For example, clips 10 for use with patients above a certain weight and/or age (such as 30 pounds or 2 years of age) may be so indicated by type or color coding. For instance, all or a portion of the clip 10 may be color coded red if the clip is intended for use with patients whose weight is less than 25 pounds while corresponding clips that are intended for use with patients over 25 pounds may have all or a portion of the corresponding clip color coded blue. Similarly, other usage related information that may be indicated on the clip 10 include, but are not limited to, patient factors such as age, gender, or pre-existing medical conditions (such as diseases or genetic predispositions).

In addition, non-usage related information may also be indicated or provided on the clip 10. For example, manufacturing information or point of origin information (such as the country in which the clip 10 was manufactured) may be indicated on the clip 10 by text or color-coding. In this manner, the manufacturer and/or country of origin may be determined for a clip 10. Likewise, other non-usage information that may be of interest may be provided on the clip 10.

The clip 10 may be formed from any suitable material that provides sufficient strength and/or resilience. Examples of suitable materials include, but are not limited to, plastics and metals. In certain embodiments the clip 10 may be formed from polypropylene or from acrylonitrile butadiene styrene (ABS). In general, the material from which the clip 10 is formed may be chosen based on suitability for the intended use (e.g., sufficiently strong to function as a physical stop to plunger withdrawal, sufficiently resilient to withstand repeated engagement and disengagement with a complementary feature of the syringe) and on suitability for the desired method of fabrication. Examples of suitable fabrication methods include, but are not limited to, three-dimensional (3-D) printing, injection molding, stamping, laser cutting with routing, and so forth.

As depicted in FIGS. 2 and 3, the elongated portion 12 may be shaped to conform to structural features typically found in a syringe. For example, in the depicted example, a surface of the elongated portion 12 may have a curved or rounded surface 22 generally corresponding to the inner surface of the barrel of a syringe with which the clip 10 is configured to be used. The curvature and/or extent of the surface 22 may vary depending on the type and/or size of syringe with which the clip 22 is to be used. Likewise, in other embodiments, the surface may be shaped differently (i.e., not rounded or curved), depending on usage or design considerations.

Further, in the depicted embodiment the inward facing surface 24 of the clip 10 is angled so as to generally conform to or fit between perpendicular structural elements that may be present on a plunger of a syringe assembly. That is, to the extent that perpendicular structural elements of a plunger form what is essentially a corner shaped niche, the inward facing surface 24 of the clip 10 may be angled or curved so as to fit within or generally conform to the perpendicular surfaces of the plunger. As will be appreciated, in different embodiments the inward facing surface 24 may be angled, as depicted, or may be rounded, curved, or have other shapes and still achieve a suitable conforming fit within a syringe assembly. In other embodiment, the cross-section of the elongated portion 12 may be generally round, triangular, square, rectangular, pentagonal, hexagonal, and so forth. In general, the elongated portion 12 may have any cross-section that allows the elongated portion to fit between the plunger and inner barrel surface of a syringe assembly and, in certain embodiments, allows rotation of the clip between locked and unlocked configurations within the syringe.

Figure 4:
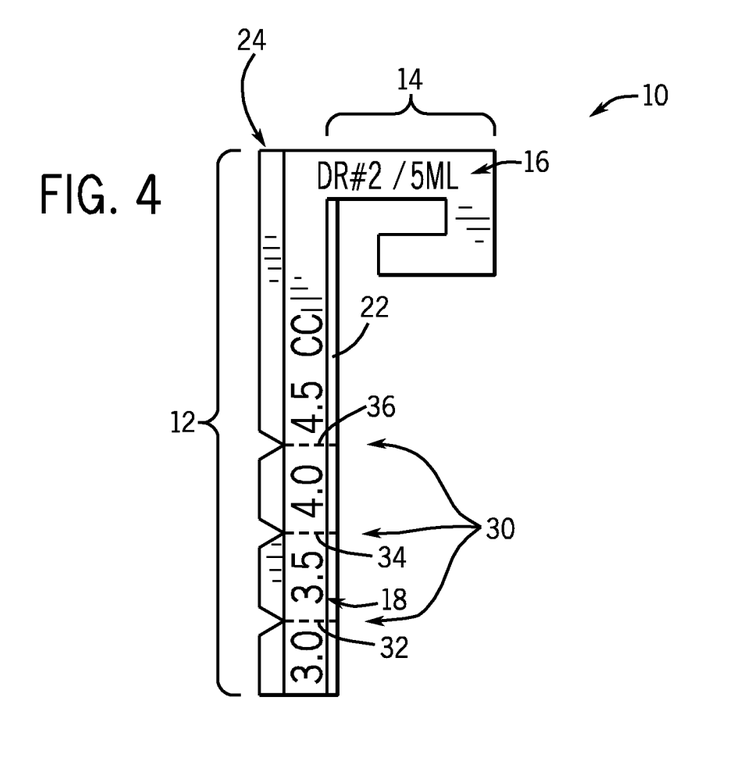
FIG. 4 depicts a plan view of one embodiment of a clip that is scored along an elongated portion to facilitate breakage along the elongated portion, in accordance with aspects of the present disclosure.

Turning to FIG. 4, an additional embodiment is depicted in which the elongated portion 12 of the clip 10 is scored or otherwise structurally weakened at one or more break points 30. In this embodiment, a single clip 10 may be adapted to provide a specified dose by breaking off the elongated portion at the appropriate location. For example, in an unaltered state the clip 10, when inserted and secured within a syringe assembly, may allow a first dose amount (e.g., 3.0 cc) to be drawn into the syringe assembly. By breaking the elongated portion at a first break point 32, a second dose amount (e.g., 3.5 cc) may be drawn into the syringe assembly. Similarly, breaking the elongated portion at a second break point 34 or at a third break point 36 allows a third dose amount (e.g., 4.0 cc) or a fourth dose amount (e.g., 4.5 cc), respectively, to be drawn into the syringe assembly. In this way, a single clip may be configured to provide different doses when integrated with a syringe assembly. As depicted, some form of visual indication 18 may be provided that corresponds to each break point so that a user can determine what doses are associated with breaking or not breaking the clip 10 at a respective break point 30.

Figure 5:
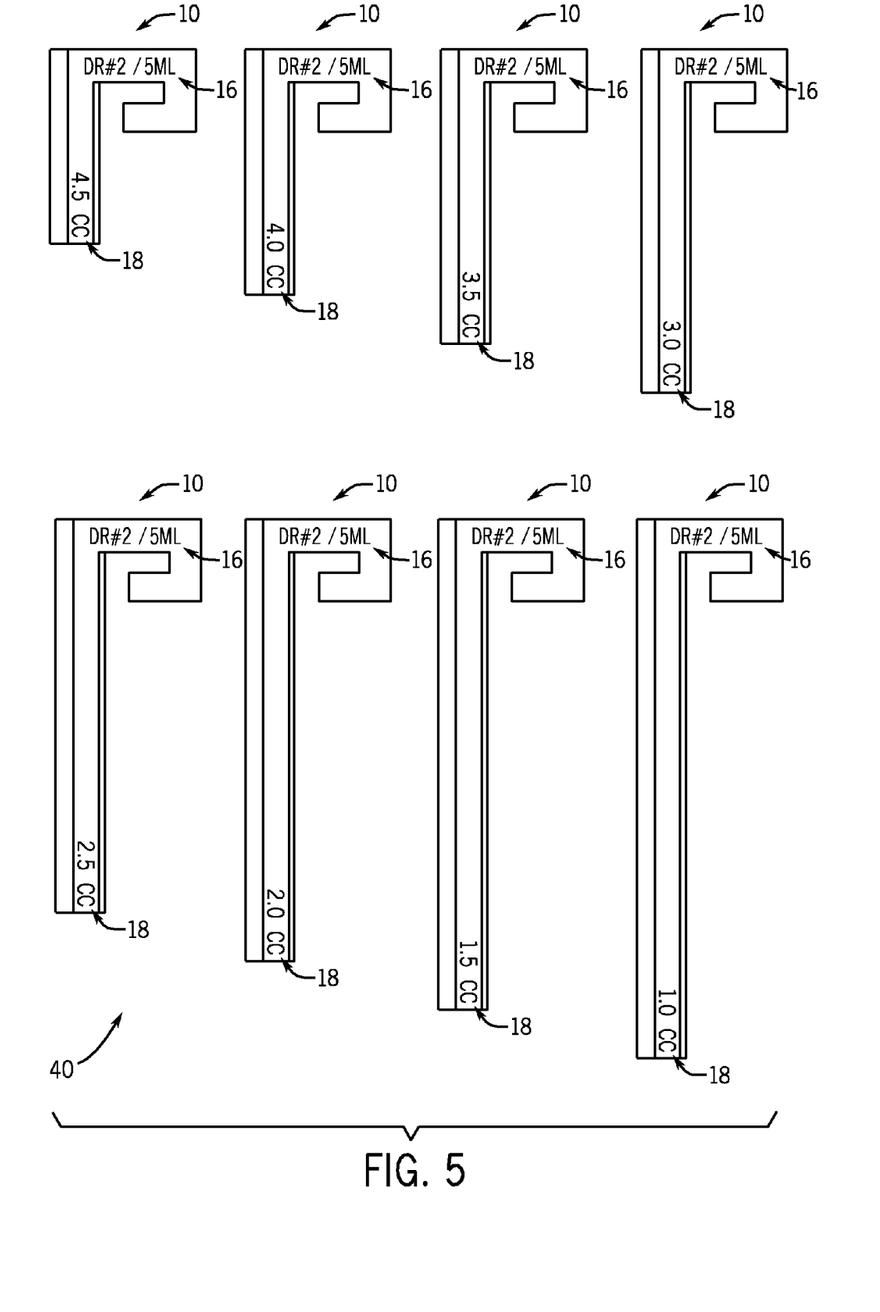
FIG. 5 depicts an assortment of clips associated with different respective doses, in accordance with aspects of the present disclosure.

Turning to FIG. 5, a kit 40 of dosing clips 10 is depicted in which different clips 10 correspond to different doses or otherwise different uses (such as based on weight, age, or patient or other patient or usage based criteria, as discussed above). For example, in one such embodiment, the elongated portion 12 of each clip 10 of the kit 40 may differ in length to correspond to the dose associated with the respective clip 10. The locking portion 14 of each clip, however, may be the same size where the clips 10 are configured for use with the same size or type of syringe.

In the depicted kit 40 each clip 10 may include indications or markings, as discussed above, indicating the dose to which each clip corresponds and/or what type, size, or style of syringe with which the clip 10 is to be used. In practice, such a kit 40 of clips 10 may be provided to a practitioner (e.g., a pharmacist or physician) to provide a range of clip sizes or usages for use by the practitioner. For example, such a kit may include clips 10 for commonly prescribed oral doses administered by a syringe. For example, the clips 10 may correspond to doses in any conventional dosing unit (e.g., cubic centimeters (cc), milliliters (mL), tablespoons, teaspoons) and may include clips 10 corresponding to conventional dosing increments within the respective unit of measurement. For example, in one embodiment, the kit 40 may include clips 10 corresponding to doses between 1.0 mL to 4.5 mL in 0.5 mL increments.

Figure 6:
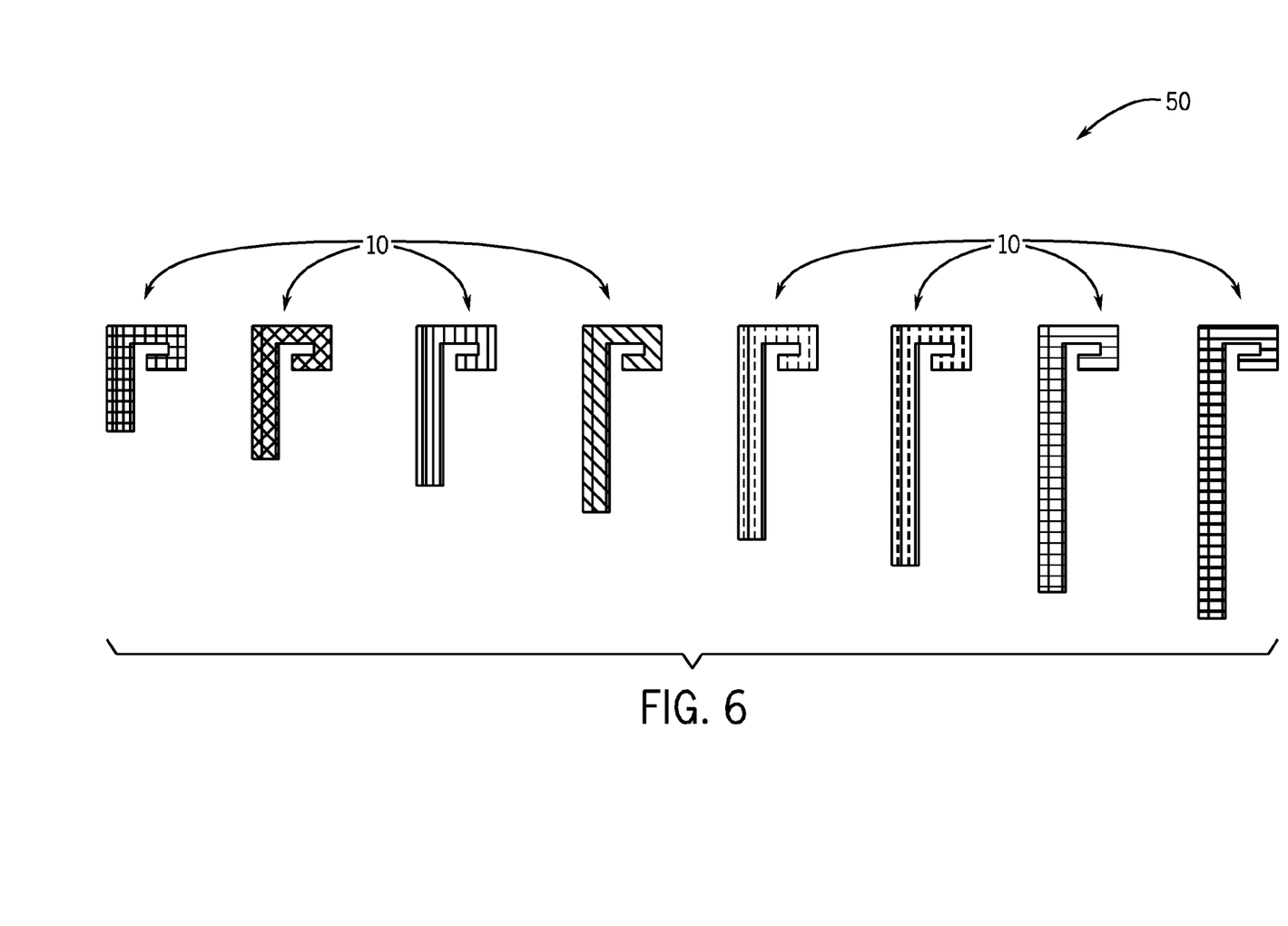
FIG. 6 depicts an assortment of color-coded clips associated with different respective doses, in accordance with aspects of the present disclosure.

Likewise, FIG. 6 depicts an alternative embodiment of a kit 50 of clips 10 of different sizes and/or for different uses. The clips 10 of the kit 50 of FIG. 6 are differentiated from one another based on color (represented in FIG. 6 by different types of hatching). In this manner, a practitioner may select a suitable clip 10 from the kit 50 by selecting a clip 10 of a color that corresponds to a desired dose or use.

As will be appreciated, the clips 10 of the respective kits depicted by FIGS. 5 and 6 are described as being distinguished by textual indications or by color to simplify explanation. However, in practice, any number or combination of visual indications may be employed in such a kit such that the indications are not limited to color or text. Likewise, in practice, color, text, and/or other visual indications may be combined and/or employed within the same kit. That is, the clips 10 of a kit may include textual and color indications of a dose to which each clip corresponds and/or the type of syringe with which each clip 10 is to be used and may also be color-coded based on dose or other use considerations. For example, in one implementation the clips 10 of a kit may include textual indications of the dose to which each clip corresponds and the type of syringe with which each clip 10 is to be used while a portion of each clip 10 (such as elongated portion 12) may also be color-coded to indicate the dose to which each clip corresponds, and a different portion of each clip 10 (such as locking portion 14) may be color-coded to indicate the weight range of patients with which the clip 10 is to be used. In this manner, different types of use indicators may be utilized to allow clips 10 within a kit to be readily distinguished from one another based on does or other use criteria.

Figure 7:
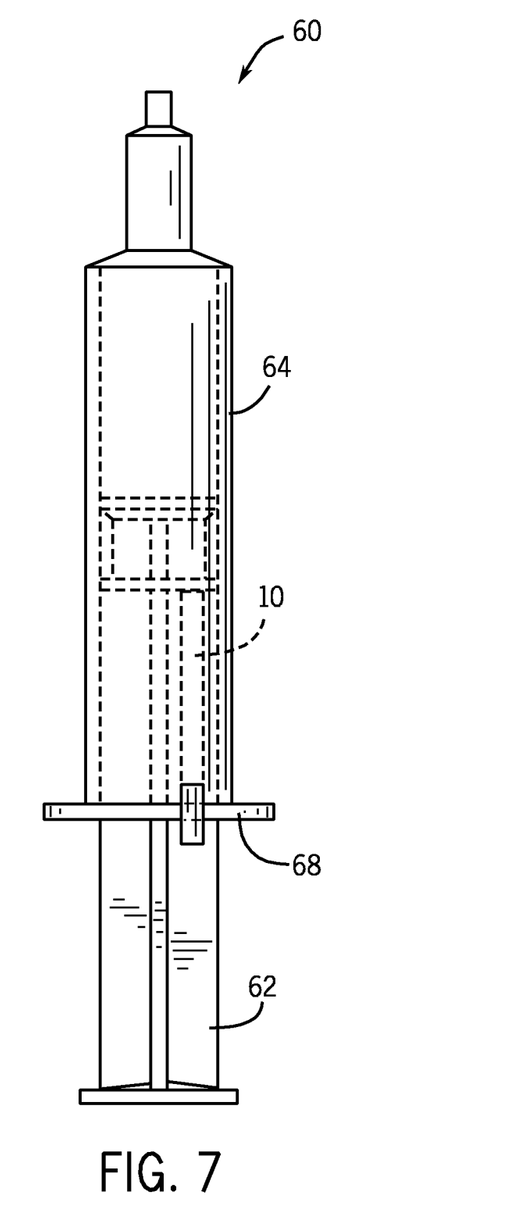
FIG. 7 depicts a side view of a syringe in which a clip has been inserted but not secured, in accordance with aspects of the present disclosure.
Figure 8:
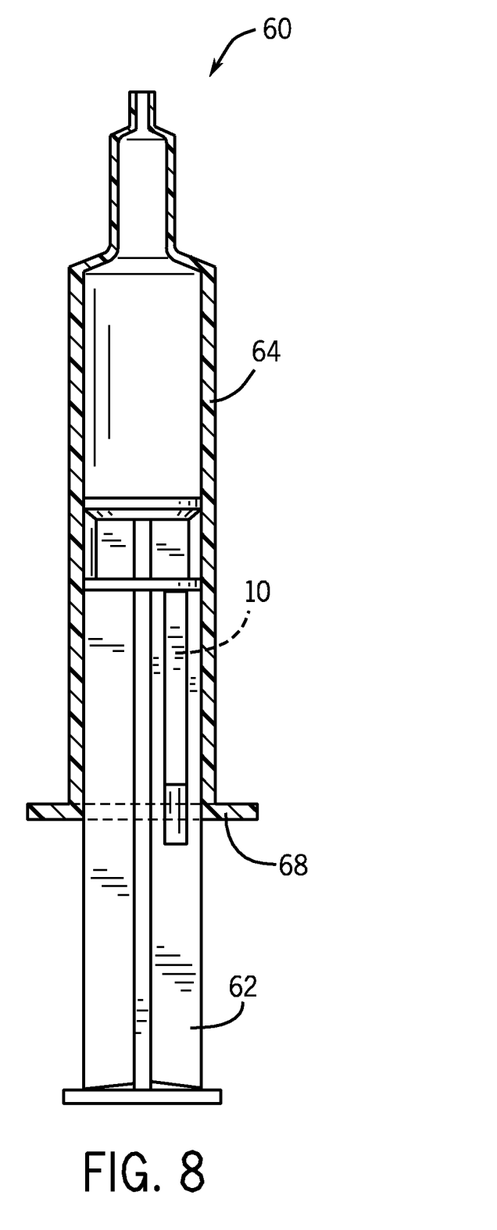
FIG. 8 is a cross-sectional view of the syringe and clip of FIG. 7 depicting the clip within the barrel of the syringe, in accordance with aspects of the present disclosure.

With the foregoing discussion of clips in mind and turning now to FIGS. 7-12, various examples of the use of a dosing clip 10 in conjunction with a syringe 60 are depicted. Turning to FIGS. 7 and 8, a clip 10 is depicted as being inserted into a syringe assembly 60 that includes a plunger 62 disposed within a barrel 64 of the syringe. In FIG. 7, the clip 10 and syringe assembly 60 are depicted from an external view while in FIG. 8 the syringe assembly 60 is partially cut-away to depict the clip 10 within the barrel 64 of the syringe 60. In the depicted example, the clip 10 is inserted into the barrel 64 of the syringe 60 but has not yet been secured to the syringe 60.

Figure 9:
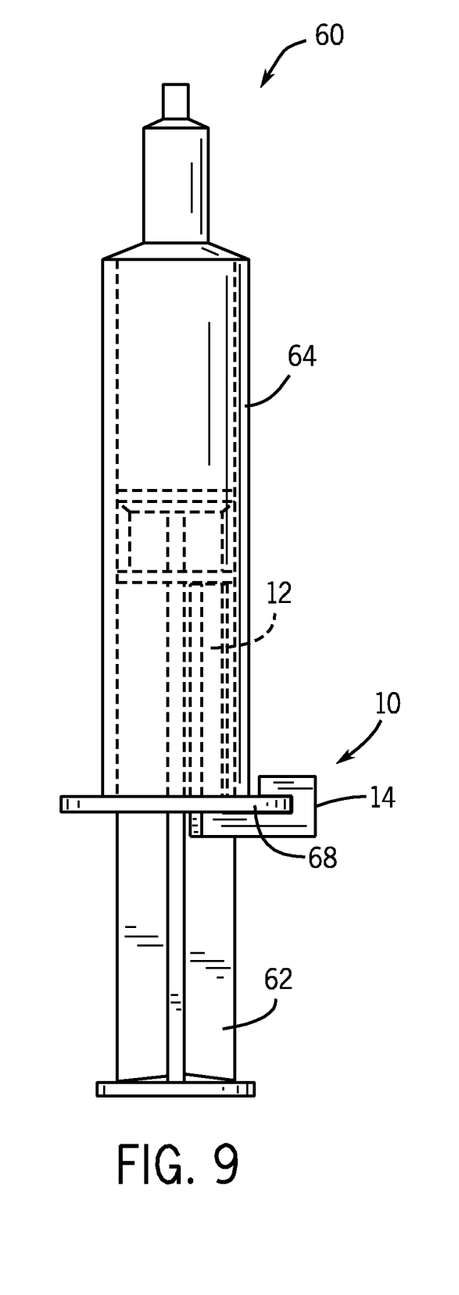
FIG. 9 depicts a side view of a syringe in which a clip has been inserted and secured, in accordance with aspects of the present disclosure.
Figure 10:
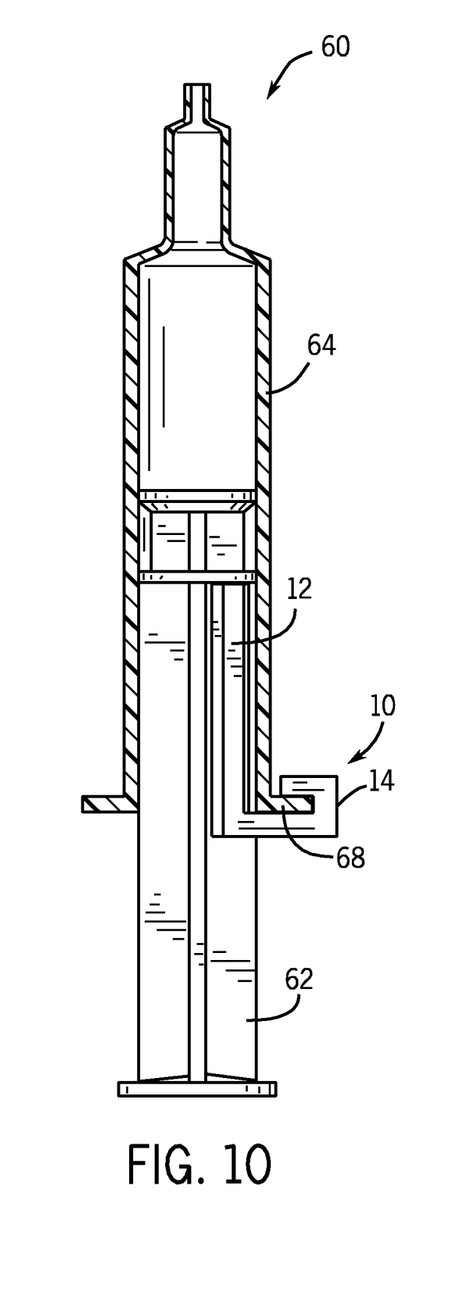
FIG. 10 is a cross-sectional view of the syringe and clip of FIG. 9 depicting the clip within the barrel of the syringe, in accordance with aspects of the present disclosure.

Turning to FIGS. 9 and 10, where FIG. 10 depicts a partial cut-away view, the clip 10 is depicted as having been rotated within the barrel 64 of the syringe 60 such that the locking portion 14 of the clip 10 is secured to a flange portion 68 of the syringe 60. In certain embodiments the flange 68 or other feature to which the clip 10 is secured may include a divot, notch, indentation, or other structure to facilitate locking of the clip 10 to the syringe 60. For example, in one such implementation, the flange 68 may include an indent or notch and the locking portion 14 of the clip 10 may be rotated to snap click into the indent, locking the clip 10 in place. Once the clip 10 is secured, the elongated portion 12 of the clip 10 physically prevents the plunger 62 from being retracted past a point that corresponds to a desired dose within the syringe 60. In this manner, a user may operate the syringe 60 by retracting the plunger 62 of the syringe 60 until the clip 10 prevents further retraction. At the point where the clip 10 prevents further retraction of the plunger 62, the syringe 60 should contain the desired dose. In certain embodiments, when it is no longer needed, the clip 10 may be rotated to disengage the flange 68 and withdrawn from the barrel 64 of the syringe 60. In other embodiments, the clip 10 may remain secured to the flange 68 (such as in embodiments where the locking portion locks or snaps into an indent or other receiving structure) such that the clip 10 is permanently associated with the syringe 60 for the life of the syringe 60.

Figure 11:
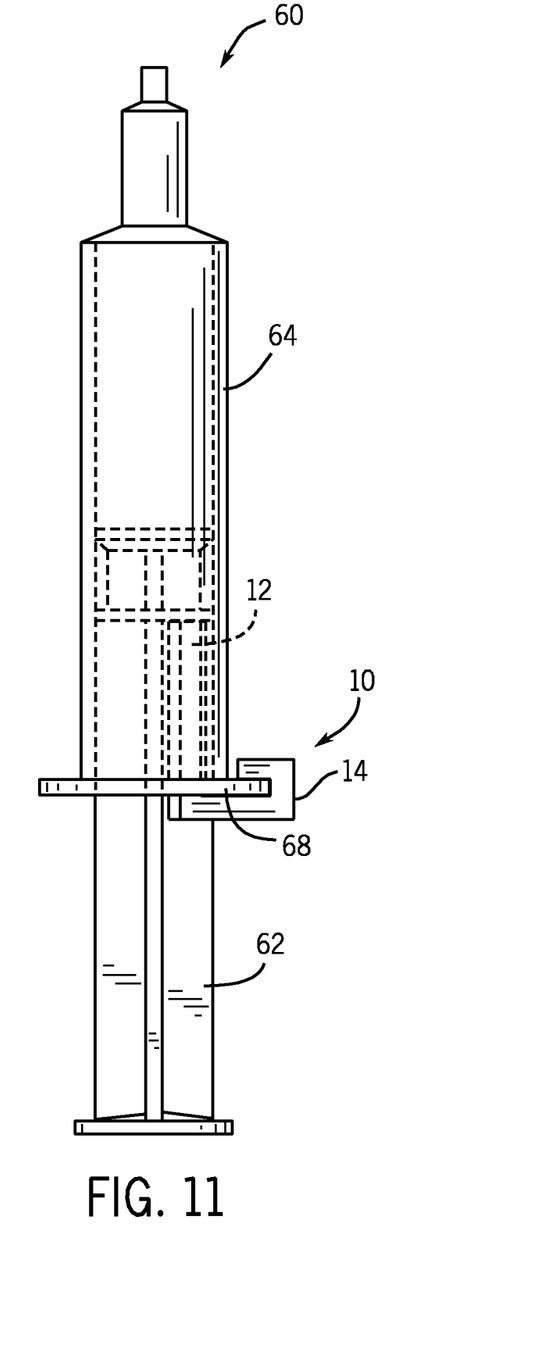
FIG. 11 depicts a side view of a syringe in which a clip corresponding to a different dosage has been inserted and secured, in accordance with aspects of the present disclosure.
Figure 12:
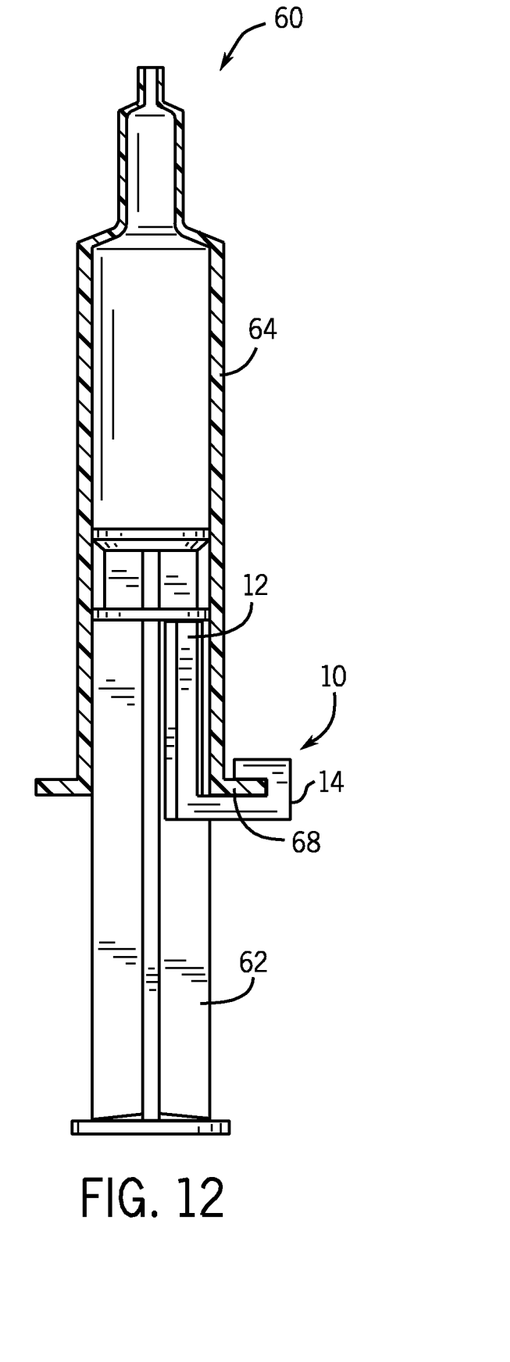
FIG. 12 is a cross-sectional view of the syringe and clip of FIG. 11 depicting the clip within the barrel of the syringe, in accordance with aspects of the present disclosure.

By way of further example, FIGS. 11 and 12, where FIG. 12 depicts a partial cut-away view, depict the use of a clip 10 having an elongated portion 12 of a different length than that depicted in FIGS. 7-10. As a result of this different length of the elongated portion 12, the plunger 62 of the syringe 60 can be retracted a different amount so that at different dose can be drawn into the syringe 60 before the clip 10 prevents further retraction of the plunger 62. In the depicted example, the clip 10 has a shorter elongated portion 12 than was depicted in FIGS. 7-10, thus allowing the plunger 62 to be retracted further before physically preventing further retraction, and thereby allowing a large dose to be drawn into the syringe 60.

With the foregoing in mind, it will be appreciated that a clip 10 of the type disclosed may be used in conjunction with a syringe, such as an oral dosing syringe, to prevent the inadvertent withdrawal of a dose in excess of what was prescribed. Likewise, greater certainty in general may be obtained in measuring a dose as the clip 10 provides a physical indication of the proper extent to which a syringe plunger should be withdrawn to measure a prescribed does into a syringe. Though discussed herein as being a separate structure from the syringe 60 and/or plunger 62, it should be appreciated that in certain embodiments the clip 10 may be constructed as an integral component of the plunger 62 or syringe 60. That is, the clip 10 may be part of the syringe 60 or plunger 62 instead of being a separate component.

In practice, the clip 10 may be used by both medical professionals as well as lay people (e.g., parents or other non-professionals). For example, in certain contexts a clip 10 may be secured to a syringe 60 by a medical professional, such as a pharmacist or physician, at a clinical treatment site or point of distribution for a pharmaceutical (e.g., a doctor's office, hospital, or pharmacy). In this manner, the doctor or pharmacist pre-configures the syringe 60 for later use by attaching a clip corresponding to the prescribed dose. A parent or layperson using the syringe configured with the clip need only withdraw medication into the syringe up to the point where the clip 10 physically prevents further withdrawal to know that the prescribed dose of medicine is present in the syringe 60.

In other contexts, such as in the context of over-the-counter medications, a manufacturer may package a medication with a syringe 60 and one or more clips 10 corresponding to the dosage instructions on the package. A person opening the package may then select the appropriate clip 10 (such as a color-coded clip where the color-coding corresponds to colors indicated in the dosage instructions) for use with the provided syringe. In this manner, a user of a syringe assembly 60 equipped with a dose clip 10 as discussed herein may fill a syringe with a prescribed dose of medication.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art, including combinations of aspects or features of the embodiments and examples disclosed herein. Such other examples are intended to be within the scope of the claims if they have structural elements that do not differ from the literal language of the claims, or if they include equivalent structural elements with insubstantial differences from the literal languages of the claims. The specific embodiments described above have been shown by way of example, and it should be understood that these embodiments may be susceptible to various modifications and alternative forms, including combinations of various features and aspects of the examples or embodiments discussed herein. It should be further understood that the claims are not intended to be limited to the particular forms disclosed, but rather to cover all modifications, equivalents, and alternatives falling within the spirit and scope of this disclosure.

The invention claimed is:

1. A clip, comprising:
an elongated portion configured to fit within the barrel of a syringe between a plunger of the syringe and an internal surface of the syringe; and
a locking portion configured to secure the clip to a feature of the syringe
wherein the elongated portion comprises an angular portion extending along a majority of a length of the elongated portion, wherein the angular portion is configured to fit within a complementary open region defined by the plunger when the clip is secured to the syringe, and wherein the elongated portion is configured to be broken at one or more scored locations to provide a particular length that corresponds to a particular dose of the syringe.

2. The clip of claim 1, wherein the elongated portion of the clip, when the clip is secured to the syringe, limits the movement of the plunger within the barrel.

3. The clip of claim 1, wherein a length of the elongated portion of the clip corresponds to a specific dose that can be measured using the syringe.

4. The clip of claim 1, wherein the locking portion comprises a C-clamp configured to be temporarily secured to the feature of the syringe.

5. The clip of claim 1, wherein the locking portion comprises a C-clamp configured to be rotated so as to engage with or disengage from the feature, the feature comprising a flange portion of the syringe that is complementary to the size and shape of the C-clamp.

6. The clip of claim 1, wherein the elongated portion comprises a rounded portion configured to complement a corresponding shape of the internal surface of the syringe when the clip is secured to the syringe.

7. The clip of claim 1, wherein one or both of the elongated portion and the locking portion comprise metal or plastic.

8. The clip of claim 1, wherein one or both of the elongated portion and the locking portion comprise polypropylene or acrylonitrile butadiene styrene (ABS).

9. The clip of claim 1, comprising a first visual indicator of the dose for which the clip corresponds and a second visual indicator of the specified size or capacity of the syringe with which the clip is configured to be used.

10. A set of dosing devices, comprising:
a plurality of syringe inserts for a specified size or capacity of a syringe, each syringe insert comprising:
an elongated portion configured to be inserted into the barrel of the syringe, wherein the elongated portion of each syringe insert is of a different length, and wherein the elongated portion comprises an angular portion extending along a majority of a length of the elongated portion, wherein the angular portion is configured to fit within a complementary open region defined by a plunger when the syringe insert is secured to the syringe;
a locking portion configured to mate with a corresponding feature of the syringe and to secure the syringe insert to the syringe when so mated; and
a first visual indicator of the dose for which the respective syringe insert corresponds; and
a second visual indicator of the specified size or capacity of the syringe with which the plurality of syringe inserts are configured to be used.

11. The set of dosing devices of claim 10, wherein the first visual indicator comprises raised type indicating the dose for which the respective syringe insert corresponds.

12. The set of dosing devices of claim 10, wherein the first visual indicator comprises a respective color used to indicate the dose for which the respective syringe insert corresponds.

13. The set of dosing devices of claim 10, wherein each syringe insert comprises a further visual indicator conveying use information for the respective syringe insert.

14. The set of dosing devices of claim 13, wherein the use information indicates a sex, a weight range, an age, or other non-dosage factors.

15. The set of dosing devices of claim 10, wherein the first visual indicator and the second visual indicator comprise textual markings disposed on the elongated portion, the locking portion, or a combination thereof.

* * * * *